United States Patent [19]

Meyer et al.

[11] Patent Number: 4,510,288

[45] Date of Patent: Apr. 9, 1985

[54] CYCLIC AMIDINES, A PROCESS FOR THEIR PRODUCTION AND THEIR USE AS CATALYSTS IN THE HARDENING OF EPOXIDE RESINS

[75] Inventors: Rolf-Volker Meyer; Hans-Joachim Kreuder; Erwin Hohl, all of Krefeld, Fed. Rep. of Germany

[73] Assignee: Bayer Aktiengesellschaft, Leverkusen, Fed. Rep. of Germany

[21] Appl. No.: 475,710

[22] Filed: Mar. 16, 1983

[30] Foreign Application Priority Data

Mar. 26, 1982 [DE] Fed. Rep. of Germany ....... 3211301

[51] Int. Cl.³ .................... C08L 59/58; C07D 239/02
[52] U.S. Cl. ..................................... 525/111; 525/375; 525/397; 525/438; 525/486; 525/533; 528/94; 544/242; 544/253; 544/335
[58] Field of Search ................ 528/94; 544/242, 335, 544/253; 525/111, 375, 397, 438, 486, 533

[56] References Cited

U.S. PATENT DOCUMENTS

| | | | |
|---|---|---|---|
| 4,044,009 | 8/1977 | Panzer et al. | 544/335 |
| 4,258,186 | 3/1981 | Schott et al. | 544/253 |
| 4,424,353 | 1/1984 | Meyer et al. | 544/253 |

FOREIGN PATENT DOCUMENTS 120622  9/1980  Japan ...................... 528/94

Primary Examiner—John Kight
Assistant Examiner—Kriellion Morgan
Attorney, Agent, or Firm—Connolly and Hutz

[57] ABSTRACT

Cyclic amidines which are modified by the incorporation of additional polar groups, may be used as catalysts for hardening heat-curable resin compositions comprising polyepoxides and optionally carboxyl group-containing polymers. Such amidine catalysts yield a high reactivity, an excellent storage stability and result in elastic coatings which show a high gloss and a good resistance to solvents.

6 Claims, No Drawings

CYCLIC AMIDINES, A PROCESS FOR THEIR PRODUCTION AND THEIR USE AS CATALYSTS IN THE HARDENING OF EPOXIDE RESINS

This invention relates to new cyclic amidines which, in addition to the

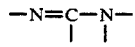

-function, also contain polar groups, to a process for the production of these amidines and to their use as catalysts in the hardening of epoxide resins, i.e. thermosetting compositions based on polyepoxides and, optionally, polymers containing carboxyl groups.

Powder-form coating compositions which may be applied to substrate by fluidisation dip coating, by flame spraying or by electrostatic power spraying are known. They are intended to be able to form crosslinked coatings after stoving for short times at moderately high temperatures. In this connection, it is important to ensure that, on the one hand, no reaction between the resin and the hardener occurs during extrusion of the mixture of binder, pigments, fillers and, optionally, other auxiliaries at temperatures in the range from 80° to 160° C. and preferably at temperatures in the range from 90° to 120° C. and, on the other hand, to remember that there is a demand for increasingly shorter stoving times at low temperatures, i.e. for increased reactivity.

Although it is possible to provide the resin component with sufficient carboxyl groups that a complete reaction is obtained under stoving conditions of 30 minutes at 150° to 160° C., but the large number of acid groups present gives rise during the actual extrusion process to an undesirable preliminary reaction which can only be kept within acceptable limits by intensive cooling of the extrudate. Stability in storage, too, is adversely affected by the fact that, even at room temperature, there is an undesirable reaction which impairs the levelling of the powder lacquer and/or the mechanical properties of the stoved lacquer.

It is known that the hardening of carboxyl-containing polymers with polyepoxides can be accelerated by catalysts, such as dicyanodiamides or heterocyclic nitrogen compounds, for example imidazolines (DE-OS No. 22 48 776) or tetrahydropyrimidines (DE-OS No. 27 51 805).

In addition to adequate reactivity and stability in storage, epoxide resin coatings are also intended to show firm adhesion, particularly to metal substrates. Difficulties in this respect are caused in particular by diglycidyl ethers of bisphenol A having a melting point of from 50° to 120° C. and an epoxide equivalent weight of from 400 to 2000. However, coating compositions will only become competitive in practice not only when they are reactive and stable in storage and lead to firmly adhering coatings, but also when the coatings produced from them show high gloss, elasticity and resistance to solvents.

It has now been found that all the desirable properties mentioned above are promoted if the amidines used as catalysts are modified by the incorporation of additional polar groups. This is all the more surprising insofar as it could not be predicted that coating properties normally determined by the choice of the resin components can be influenced at all, let alone significantly, by the hardening catalyst used.

The present invention relates to a process for hardening epoxide resins using catalysts represented by formula (1):

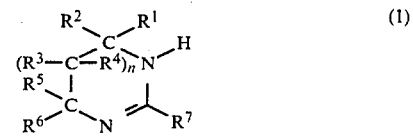

in which
$n_1 = 0$ or 1,
$R^1$ to $R^6$ independently of one another represent a hydrogen atom or a $C_1$-$C_4$-alkyl, $C_5$-$C_{10}$-cycloalkyl, $C_7$-$C_{13}$-aralkyl or $C_6$-$C_{18}$-aryl group or two substituents $R^1/R^2$, $R^3/R^4$, $R^5/R^6$, $R^1/R^3$ or $R^1/R^5$ together represent a $C_1$-$C_5$-alkylene radical,
$R^7$ represents an aliphatic, cycloaliphatic, araliphatic or aromatic radical containing from 1 to 36 carbon atoms which is either substituted by OH, COOH, $OR^8$, $NR^9R^{10}$ or interrupted by a keto group or by 1 to 10 amide or ester groups, or a polyester radical having the structure

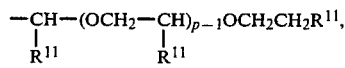

$R^8$ represents a $C_1$-$C_{15}$-alkyl or a $C_6$-$C_{19}$-aryl group,
$R^9$ and $R^{10}$ independently of one another represent a hydrogen atom, or $C_1$-$C_{12}$-alkyl group, $C_6$-$C_8$-cycloalkyl group or both substituents together represent $C_4$-$C_6$-alkylene,
$R^{11}$ represents a hydrogen atom, a $C_1$-$C_4$-alkyl group, or a phenyl group and
p is a number of from 1 to 40,
as catalysts for the hardening of, preferably pulverulent epoxide resins.

Preferred compounds (1) are substituted imidazolines and substituted tetrahydropyrimidines, but particularly amidines corresponding to the following formula (1a)

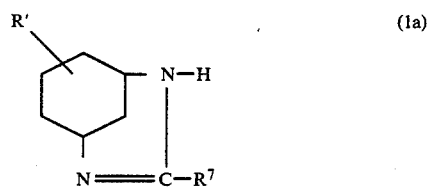

in which
$R^7$ is as defined above and
R' is a $C_1$-$C_4$-alkyl radical, preferably methyl, or a hydrogen atom.

The present invention also provides compounds corresponding to the following formula (2):

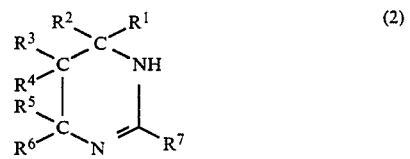

in which the substituents have the meanings previously defined.

The present invention also provides a process for the production of compounds corresponding to formula (2), characterised in that a carboxylic acid of the formula $R^1$—COOH or a reactive carboxylic acid derivative thereof is reacted with from 1.0 to 2.5 and preferably with from 1.0 to 1.5 moles, based on 1 mole of carboxylic acid (derivative) used, of a diamine corresponding to formula:

$$H_2N-C(R^1R^2)-C(R^3R^4)-C(R^5R^6)-NH_2$$

at a temperature in the range from 150° to 280° C. and preferably at a temperature in the range from 200° to 250° C.

Preferred carboxylic acids $R^7$—COOH for the production of compounds corresponding to the formula (1) are, for example, hydroxy carboxylic acids, for example lactic acid, ricinoleic acid, 12-hydroxy stearic acid, 9,10-dihydroxy stearic acid and hydroxy benzoic acids; dicarboxylic acids such as, for example, adipic acid, azelaic acid, isophthalic and terephthalic acid; amino acids, for example, glycine, alanine, sarcosine, valine, aminocaproic acid, leucine and isoleucine; ether carboxylic acids and polyether carboxylic acids; ketocarboxylic acids, for example, levulinic acid and benzophenone carboxylic acids; carboxylic acids containing amide groups corresponding to the following formula (3):

$$HO_2C-R^{12}-C-[NH-R^{13}-NH-CO-R^{14}-C]_q-NH-R^{15}$$
$$\phantom{HO_2C-R^{12}-}\|\phantom{-[NH-R^{13}-NH-CO-R^{14}-C]_q-NH-R^{15}}\|$$
$$\phantom{HO_2C-R^{12}-}O\phantom{-[NH-R^{13}-NH-CO-R^{14}-}O$$
(3)

in which q = 0 or is an integer of from 1 to 10 and preferably 0 or an integer from 1 to 4, $R^{12}$ to $R^{14}$ independently of one another represent difunctional aliphatic $C_2$-$C_{20}$, preferably $C_4$-$C_{10}$ hydrocarbon radicals, or aromatic $C_6$-$C_{19}$, preferably $C_6$-$C_{15}$-hydrocarbon radicals, $R^{13}$ preferably representing $C_6$-alkyl, $C_6$-$C_{15}$-cycloalkyl or $C_6$-$C_{13}$ aryl, $R^{15}$ represents a monofunctional $C_1$-$C_{18}$-alkyl radical or a $C_6$-$C_{15}$-aryl radical;

carboxylic acids containing ester groups corresponding to the following formula (4):

$$HO_2C-R^{12}-C-[OR^{13}OCR^{14}C]_qOR^{15}$$
$$\phantom{HO_2C-R^{12}-}\|\phantom{-[OR^{13}OCR^{14}}\|$$
$$\phantom{HO_2C-R^{12}-}O\phantom{-[OR^{13}O}O$$
(14)

in which q and the radicals $R^{12}$ to $R^{15}$ are as previously defined, although $R^{12}$, $R^{14}$ independently of one another preferably represent a difunctional aliphatic $C_2$-$C_{10}$-radical or a $C_6$-aryl radical, $R^{13}$ represents a difunctional aliphatic $C_2$-$C_6$-radical and $R^{14}$ represents a difunctional aliphatic $C_1$-$C_{18}$-radical.

In the case of binuclear aromatic dicarboxylic acids, the nuclei may be connected by an oxygen atom, a keto group, a sulfo group or a $C_1$-$C_4$-alkylene group.

The above-mentioned polyether carboxylic acids preferably correspond to the following formula:

$$R^{11}CH_2CH_2O{-}(CH{-}CH_2O)_{p-1}{-}CH{-}COOH$$
$$\phantom{R^{11}CH_2CH_2O{-}(}|\phantom{CH{-}CH_2O)_{p-1}{-}}|$$
$$\phantom{R^{11}CH_2CH_2O{-}(}R^{11}\phantom{CH{-}CH_2O)_{p-1}{-}}R^{11}$$

and may be obtained by the cyanoethylation or polyether diol monoalkyl ethers, followed by hydrolysis of the nitrile, and also by oxidation of the OH group of such polyether diol monoalkyl ethers (for example with permanganate, chromic acid anhydride, hydrogen peroxide and catalysts and peroxides).

Preferred diamines for the production of compounds corresponding to formula (1) are aliphatic and cycloaliphatic 1,2- and 1,3-diamines, particularly ethylene diamine, 1,2-propylene diamine, 1,3-propylene diamine, 1,3-diaminocyclohexanes and, more preferably, the various methyl-1,3-diaminocyclohexane isomers which may be obtained by hydrogenation of the tolylene diamine isomeric mixtures readily obtainable on a commercial scale.

An excess of diamine has proved to be advantageous because it depresses the formation of secondary products, particularly diamides. In some cases, it is advisable to use a catalyst.

The reaction may be terminated when no more of the carboxylic acid (derivative) used can be detected and excess diamine has been distilled off. This is generally the case after from 2 to 10 hours.

In many cases, the amidines of formula (1) obtained may be used without further purification because the secondary products formed (amidoamines, diamides) do not significantly affect the catalytic activity of the amidine components.

Where practicable, a reversible reaction with polyisocyanates or, preferably, monoisocyanates can be of assistance in increasing the melting point of the compounds corresponding to formula (1); in this way, the crosslinking of the powder lacquers is displaced to higher temperatures.

The catalysts according to the invention are used in quantities of from 0.1 to 5% by weight and preferably in quantities of from 1 to 2% by weight, based on the sum of epoxide resin and the acid polymers optionally present. The addition is preferably made in a single step during the production of the final powder lacquer system by extrusion.

The polyepoxides which may be used in accordance with the invention are solid, generally resin-like substances which melt at temperatures in the range from 30° to 140° C. and preferably at temperatures in the range from 40° to 80° C. (as determined by differential thermoanalysis) and which on average contain more than one 1,2-epoxy group per molecule.

The polyepoxide compounds in question are, on the one hand, polyepoxide compounds based on polyhydric phenols, for example of pyrocatechol, resorcinol, hydroquinone, of 4,4'-dihydroxy diphenyl methane, of 4,4'-dihydroxy-3,3'-dimethyl diphenyl methane, of 4,4'-dihydroxy diphenyl dimethyl methane (bisphenol A), of 4,4'-dihydroxy diphenyl methyl methane, of 4,4'-dihydroxy-3,3'-dihydroxy diphenyl cyclohexane, of 4,4'-dihydroxy diphenyl propane, of 4,4'-dihydroxy diphenyl sulfone, of tris-(4-hydroxy-phenyl)-methane, of the chlorination and bromination products of the above-mentioned diphenols, particularly of bisphenol A; of novolacs (i.e. of reaction products of monohydric or polyhydric phenols with aldehydes, particularly formaldehyde, in the presence of acid catalysts), of diphenols obtained by esterifying 2 moles of the sodium salt of an aromatic oxycarboxylic acid with 1 mole of dihaloalkane or dihalodialkyl ether (cf. British Pat. No. 1,017,612), of polyphenols obtained by the condensation of phenols and long-chain halogen paraffins containing at least 2 halogen atoms (British Pat. No. 1,024,288).

It is preferred to use standard commercial solid epoxide resins of the category of diglycidyl ethers of bisphenol A (i.e. reaction products of bisphenol A with epichlorohydrin) of which the epoxide equivalent weight is in the range of from 400 to 2500.

It is also possible to use such compounds as (poly)-glycidyl esters corresponding to the following formula (5)

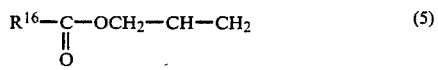

in which
R$^{16}$ represents a linear or branched, saturated or unsaturated hydrocarbon radical containing from 4 to 20 carbon atoms or an optionally substituted phenyl radical.

Other suitable epoxide resins are compounds such as triglycidyl isocyanurate and/or its oligomers and triglycidyl urazole and its oligomers, also mixtures of compounds from the above-mentioned categories.

The polymers containing carboxyl groups may be polyester polycarboxylic acids produced from polyols and polycarboxylic acids or derivatives thereof.

The polymers containing carboxyl groups should have a melting and softening range as (determined by differential thermoanalysis) of from 20° C. to 150° C. and preferably from 50° C. to 100° C. and an acid number of from 10 to 150, preferably from 20 to 120 and, more particularly, from 30 to 50. The OH—numbers should preferably be below 20 and, more particularly, below 10.

The esterification reaction by which the polyester carboxylic acids are formed may be carried out in known manner by esterifying corresponding polycarboxylic acids and polyols, particularly dicarboxylic acids and dialcohols, or by ester formation from suitable derivatives of these alcohols and carboxylic acids, such as for example anhydrides, acid chlorides, and even with hydroxy carboxylic acids.

Particularly preferred, branched, i.e. at least trisfunctional, polyester polycarboxylic acids are obtained by the incorporation of at least trifunctional polycarboxylic acids or their anhydrides, such as benzene-1,3,5-tricarboxylic acid or trimellitic acid anhydride.

The molar mixing ratio of polymers containing carboxyl groups to epoxide resin is generally selected such that there are from 0.6 to 1.5 and preferably from 0.8 to 1.25 epoxide groups for each free carboxyl group.

Powder lacquer auxiliaries and additives, for example, pigments, dyes, fillers, levelling agents, thixotropising agents, aerating agents, UV-stabilisers, oxidation inhibitors and quenchers (radical interceptors such as, for example, N-alkyl-substituted piperidines), also matting agents and agents of the type which improve surface smoothness, may of course be incorporated in the conventional manner.

The production of powder lacquers is normally carried out as follows:

The polymer containing carboxyl groups is first mixed with the polyepoxide selected and other additives, if any, and homogenised in the melt. This may be done in suitable units, for example, heatable kneaders, but preferably by extrusion, the extrusion temperature being selected such that maximum shear acts on the mixture. The temperature should not exceed an upper limit of 140° C.

After cooling to room temperature and after suitable preliminary size-reduction, the extruded mass is ground to form a powder lacquer with average particle sizes to from about 40 to 90 μm but preferably in the order of 50 μm being desirable, depending on the application envisaged. Any coarse particles present (particles larger than 90 μm) are removed by sifting.

The powder lacquers thus produced may be applied to suitable substrates by any of the usual methods, for example electrostatic powder spraying, fluidisation dip coating, electrostatic dip coating and by flame spraying or even by the application of aqueous suspensions by conventional or electrical methods.

After the powder lacquer has been applied by one of the above-mentioned processes, the coated specimen are heated to temperatures of 140° C. or higher for hardening, the heating time depending essentially on the thermal capacity of the coated specimen or on its temperature before coating.

Many of the polar-modified amidines are highly soluble in solvents, for example, benzyl alcohol (far better than the non-polar-modified analogues), and may also be very effectively used in this form as hardening catalysts for liquid epoxy systems. The COOH— and OH— modified amidines of formula (1) may readily be dispersed in water and, accordingly, may also be used in environmentally compatible aqueous coating systems.

The parts and ratios quoted in the following Examples are based on weight, unless otherwise indicated.

EXAMPLE 1

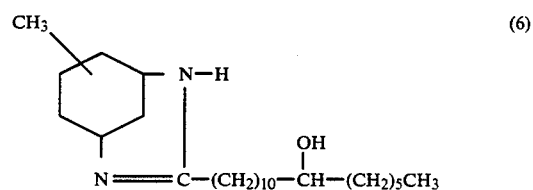

64 g (0.5 mole) of methyl-2,4-diaminocyclohexane (isomeric mixture), hereinafter referred to as "PH-tolamine" and 80 g (0.25 mole) of 12-hydroxy stearic acid were introduced under nitrogen into a 250 ml three-necked flask equipped with a stirrer, thermometer and Claisen bridge with a 100 ml capacity receiving flask. The contents of the flask were then vigorously heated with stirring to 250° C., water and excess PH-tolamine distilling off. The reaction ceased after a reaction time of 4 hours at 250° C.

In addition to 39.6 g of distillate (excess PH-tolamine and water), 104 g of a brownish wax having a softening range around 40° C. were obtained; this wax could be used without further purification as a hardening catalyst.

EXAMPLE 2

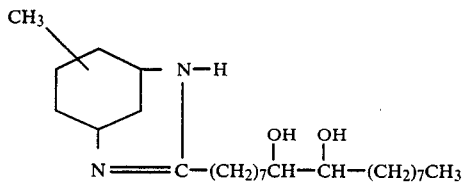

(7)

77 g (0.6 mole) of PH-tolamine and 116 g (0.35 mole) of 9,10-dihydroxy stearic acid were reacted with one another over a period of 4 hours at 250° C. as described in Example 1. In addition to 61 g of distillate, 131.5 g of a yellow resin were obtained.

EXAMPLE 3

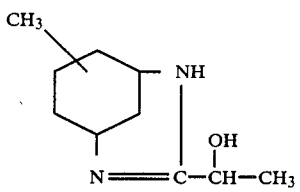

(8)

190 g (1.5 mole) of PH-tolamine were introduced with stirring under nitrogen into a 500 ml capacity three-necked flask equipped with a stirrer, thermometer, dropping funnel and Claisen bridge with a 250 ml capacity receiving flask. 100 g (1 mole) of aqueous lactic acid (90%) were introduced in portions over a period of 15 minutes, the temperature rising to 105° C. The reaction mixture was then rapidly heated to 250° C., water and excess PH-tolamine distilling off. The reaction was ceased after 4 hours at 250° C. 143 g of distillate (PH-tolamine and water) and 145 g of a red-brown cystalline reaction product melting at 50° C. were obtained. The reaction product could be used without further purification as a hardening catalyst.

EXAMPLE 4

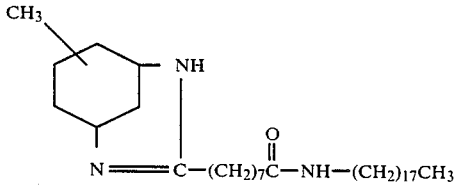

(9)

190 g (1.5 moles) of PH-tolamine were added at 80° C. to 439 g (1.0 moles) of azelaic acid stearyl amide and the resulting mixture was heated with stirring under nitrogen to a temperature of 250° C., water and excess PH-tolamine distilling off. The reaction ceased after 4 hours at 250° C. In addition to 63 g of distillate, 565 g of a pale yellow brittle resin were obtained as the reaction product (softening point around 80° C.). The reaction product can be used without further purification as a hardening catalyst.

EXAMPLE 5

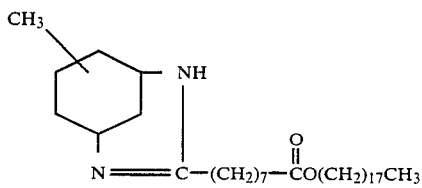

(10)

190 g (1.5 moles) of PH-tolamine were added at 80° C. to 438 g (1.0 mole) of azelaic acid monostearyl ester and the resulting mixture was heated with stirring under nitrogen to a temperature of 250° C., water and excess PH-toluene distilling off. The reaction ceased after stirring for 4 hours at 250° C. 47 g of distillate and 580 g of a light-coloured wax having a softening point of around 40° C. were obtained.

EXAMPLE 6

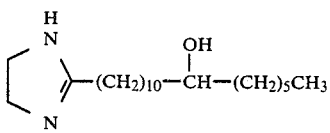

(11)

As described in Example 1, 60 g (1 mole) of ethylene diamine and 126 g (0.4 mole) of 12-hydroxy stearic acid were heated with stirring under nitrogen to 250° C., water and excess ethylene diamine distilling off. The reaction ceased after 4 hours at 250° C.

In addition to 50 g of distillate, 135 g of pale yellow crystals softening at around 110° C. were obtained. The reaction product could be used without further purification as a hardening catalyst.

Application Examples, Production of Powder Lacquers

EXAMPLE 7

60.9 parts of a carboxyl polyester of neopentyl glycol, terephthalic acid, isophthalic acid, trimellitic acid anhydride with a softening point of 75° C. (DTA) and an acid number of 35 were first dry-mixed with 0.62 part of the amidine according to Example 1 and with 4.6 parts of triglycidyl isocyanurate (corresponding to a polyester resin/epoxide hardener ratio of 93:7) and with 33.0 part of a highly stable titanium dioxide rutile and 0.4 part of a levelling agent based on a standard commercial acrylate oligomer. The resulting mixture was then dispersed in the melt using a laboratory extruder at temperatures in range from 80° to 120° C. After cooling and preliminary size reduction, the extrudate was ground in a blowing mill to an average particle size of 50 μm to form a powder lacquer. After coarse particles larger than 90 μm in size has been sifted off, the final powder lacquer was electrostatically sprayed at a negative voltage of approximately 60 kV onto twice-pickled degreased test plates (16.5 cm long, 65 mm wide, 0.8 mm thick). The test plates were then stoved at different temperatures.

The 50 μm thick coatings were then tested for their properties by the following standard methods:

| Erichsen identation | (DIN 53 156) | → | "indentation" |
| Gloss, 60° | (DIN 67 530) | → | "gloss" |
| Impact reverse | (12.7 diameter ball) | → | "IMR. 1 kg |

Acetone resistance was assessed on the following scale:

| | Example 7 | CT 1 | Example 8 | CT 2 | Example 9 | Example 10 |
|---|---|---|---|---|---|---|
| Gelling time at 180° C. (sec) | 68 | 91 | 76 | 348 | 164 | 150 |
| Indentation after 30 mins/140° C. | >10 | >10 | >10 | 0.3 | 8.0 | >10 |
| (mm) 10 mins/160° C. | >10 | >10 | >10 | 0.3 | | |
| 20 mins/160° C. | | | | | >10 | >10 |
| 15 mins/170° C. | | | | | >10 | >10 |
| IMR after 30 mins/140° C. | 150 | 80 | −5 | −5 | 10 | 5 |
| (cm/kg) 10 mins/160° C. | 120 | 10 | −5 | −5 | | |
| 20 mins/160° C. | | | | | 150 | 150 |
| 15 mins/170° C. | | | | | 140 | 140 |
| Gloss after 30 mins/140° C. | 90 | 85 | 91 | 92 | 99 | 99 |
| 60° 10 mins/160° C. | 91 | 91 | 91 | 91 | | |
| 20 mins/160° C. | | | | | 99 | 98 |
| 15 mins/170° C. | | | | | 98 | 98 |
| Acetone 30 mins/140° C. | 0-1 | 2 | 0-1 | −6 | −40 | 2 m |
| resistance after 10 mins/160° C. | 1 | 1 | 1 | −6 | | |
| 20 mins/160° C. | | | | | 2 m | 2 m |
| 15 mins/170° C. | | | | | 2 lm | 2 |
| Levelling (visual) | ← | ← | slight texture | | → | → |

| −1 ... −50 | number of strokes with an acetone-impregnated cottonwool plug before the lacquer film wears through; |
| 2 m | after 50 strokes, film matt and soft; |
| 2 lm | after 50 strokes, film slightly matt and soft; |
| 2 | soft film after 50 strokes; |
| 1 | slightly surface-sensitive lacquer film after 50 strokes; |
| 0 | no changes. |
| Levelling: | lacquer surface visually examined. |

In all the Examples and comparison tests, the lattice cut test according to DIN 53 151 produced the high rating Gt 0/0.

The test results are set out in Table 1.

EXAMPLE 8

A powder lacquer is produced as described in Example 7 using 0.62 part of the amidine of Example 6 as the catalyst.

COMPARISION TEST 1 and 2

Powder lacquers are produced in the same way as described in Example 7, except that 0.62 part of an amidine (12) (CT 1) and 0.62 parts of 2-phenyl imidazoline (CT 2) were used as catalysts.

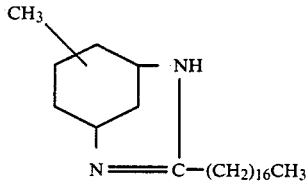
(12)

EXAMPLE 9

A powder lacquer was produced from 39.0 parts of the carboxyl polyester of Example 7, 26.0 parts of an epoxide resin having an epoxide equivalent weight of 800 and a melting range of from 90° to 100° C. (polyester/epoxide ratio 60:40) and 0.2 part of an amidamidine corresponding to Example 4 and from 33.0 part of a highly resistant titanium dioxide rutile and 0.6 part of a levelling agent based on a standard commercial acrylate oligomer.

EXAMPLE 10

A powder lacquer was produced as described in Example 9 using an ester amidine corresponding to that of Example 5.

EXAMPLE 11

A powder lacquer was produced as described in Example 7 from 62.4 parts of an epoxide resin having an epoxide equivalent weight of 800 and a melting range of 90° to 100° C. in conjunction with 4.0 parts of the amidine of Example 3, 33 parts of a highly resistant titanium dioxide rutile and 0.6 part of a levelling agent based on an acrylate oligomer.

COMPARISON TESTS 3 and 4

A powder lacquer was produced as described in Example 11, except that 4.0 parts of an amidine corresponding to formula (12) (CT 3) and 0.62 part of 2-phenyl imidazoline (CT 4) were used.

EXAMPLE 12

A powder lacquer was produced as described in Example 11 using 0.62 part of the amidine of Example 2.

EXAMPLE 13

A powder lacquer was produced as described in Example 11 from 62.4 parts of an epoxide resin having an equivalent weight of 800 and 4.0 parts of the amidine of Example 3 in conjunction with 0.2 part of an emulsifier based on ethoxylated nonyl phenol, 33.0 parts of a highly resistant titanium dioxide rutile, 6.0 parts of a polypropylene glycol (molecular weight approximately 1000) and 0.6 part of an acrylate ologomer.

This powder lacquer was dispersed in water and ground in a ball mill to a particle size of approximately 5 μm. The resulting suspension was applied to aluminium using a normal air pressure driven spray gun.

COMPARISON TEST 5

A powder lacquer suspension was produced as described in Example 13 using 4.0 parts of an amidine corresponding to formula (12).

TABLE 2

|  |  | Example 11 | CT 3 | CT 4 | Example 12 | Example 13 | CT 5 |
| --- | --- | --- | --- | --- | --- | --- | --- |
| Gelling time at 180° C. (sec) | | 50 | 75 | 35 | 35 | 50 | 75 |
| Indentation after (mm) | 30 mins/140° C. | >10 | >10 | 6.0 | 8.7 | 7.3 | 6.0 |
| | 20 mins/150° C. | >10 | 8.8 | 6.0 | 8.8 | 6.9 | 7.3 |
| | 8 mins/170° C. | >10 | 9.8 | 5.8 | 9.1 | 9.6 | 8.0 |
| IMR after (cm/kg) | 30 mins/140° C. | 130 | 5 | −5 | 150 | 5 | 5 |
| | 20 mins/150° C. | 130 | 50 | 20 | 80 | 5 | −5 |
| | 8 mins/170° C. | 80 | −5 | 60 | 60 | 5 | 5 |
| Gloss after 60° | 30 mins/140° C. | 102 | 95 | 95 | 94 | 90 | 90 |
| | 20 mins/150° C. | 101 | 95 | 95 | 91 | 90 | 89 |
| | 8 mins/170° C. | 101 | 91 | 92 | 89 | 86 | 86 |
| Acetone resistance after | 30 mins/140° C. | 0–1 | 0–1 | 0–1 | 0–1 | 1 | 1 |
| | 20 mins/150° C. | 0–1 | 0–1 | 0–1 | 0–1 | 1 | 1 |
| | 8 mins/170° C. | 0–1 | 1 | 0–1 | 0–1 | 0–1 | 1 |
| Levelling (visual) | | slight texture | texture | heavy texture | slight texture | crater-free surface | numerous craters and pin holes |

We claim:

1. Compounds corresponding to the following formula (2):

<chemical structure (2)> in which
  $R^1$ to $R^6$ independently of one another represent a hydrogen atom, a $C_1$–$C_4$-alkyl, $C_5$–$C_{10}$-cycloalkyl, $C_7$–$C_{13}$-aralkyl or a $C_6$–$C_{18}$-aryl group or two substituents $R^1/R^2$, $R^3/R^4$, $R^5/R^6$,
  $R^1/R^3$ or $R^1/R^5$ together represent a $C_1$–$C_5$-alkylene radical,
  $R^7$ represents an aliphatic, cycloaliphatic, araliphatic or aromatic radical containing from 1 to 36 carbon atoms which is either substituted by COOH or $NR^9R^{10}$, or interrupted by a keto group or by 1 to 10 amide or ester groups;
  $R^9$ and $R^{10}$ independently of one another represent a hydrogen atom or a $C_1$–$C_{12}$-alkyl or $C_6$–$C_8$-cycloalkyl group or both substituents together represent a $C_4$–$C_6$-alkylene group.

2. Compounds as claimed in claim 1, characterised in that they correspond to the following formula (1a):

<chemical structure (1a)> in which R' represents a $C_1$–$C_4$-alkyl radical or a hydrogen atom.

3. A process for producing the compounds claimed in claim 1 wherein a carboxylic acid of the formula $R^7$—COOH or a reactive derivative thereof is reacted with from 1.0 to 2.5 moles per mole of carboxylic acid or derivative of a diamine corresponding to the following formula:

$$H_2N—C(R^1R^2)—C(R^3R^4)—C(R^5R^6)—NH_2$$

at a temperature in the range from 150° to 280° C.

4. Process for hardening compositions based on polyepoxide and polymers containing carboxyl using catalysts represented by formula <chemical structure> in which
  n=0 or 1,
  $R^1$ to $R^6$ independently of one another represent a hydrogen atom,
  a $C_1$–$C_4$-alkyl, $C_5$–$C_{10}$-cycloalkyl, $C_7$–$C_{13}$-aralkyl or a $C_6$–$C_{18}$-aryl or the two substituents $R^1/R^2$, $R^3/R^4$, $R^5/R^6$, $R^1/R^3$ or $R^1/R^5$ together represent a $C_1$–$C_5$-alkylene,
  $R^7$ represents an aliphatic, cycloaliphatic, araliphatic or aromatic moiety containing from 1 to 36 carbon atoms which is either substituted by at least one —OH, —COOH, —$OR^8$, or —$NR^9R^{10}$ or interrupted by a keto moiety, by 1 to 10 amide or ester moieties or a polyether having the structure $$—CH—(OCH_2—CH)_{p-1}OCH_2CH_2R^{11},$$
$$\phantom{—CH}|\phantom{(OCH_2—CH)_{p-1}OCH_2CH_2}|$$
$$\phantom{—CH}R^{11}\phantom{(OCH_2—CH)_{p-1}OCH_2CH_2}R^{11}$$

$R^8$ represents $C_1$–$C_{15}$-alkyl, $C_6$–$C_{19}$-aryl,
  $R^9$ and $R^{10}$ independently of one another represent a hydrogen atom, a $C_1$–$C_{12}$-alkyl or $C_6$–$C_8$-cycloalkyl or both $R^9$ and $R^{10}$ together represent a $C_4$–$C_6$-alkylene,
  $R^{11}$ represents a hydrogen atom, a $C_1$–$C_4$-alkyl or phenyl, and p is a number of from 1 to 40,
which process comprises adding the catalyst to the composition to be hardened.

5. The compound as claimed in claim 1 wherein $R^1$ is methyl.

6. The compound as claimed in claim 2 wherein $R^1$ is methyl.

* * * * *